(12) United States Patent
Aykroyd et al.

(10) Patent No.: US 12,697,435 B2
(45) Date of Patent: Aug. 4, 2026

(54) NON-INVASIVE MEDICAL DEVICE EFFICIENCY AND FAULT DETECTION SYSTEMS AND METHODS OF USE

(71) Applicant: Roche Diabetes Care, Inc., Indianapolis, IN (US)

(72) Inventors: Timothy N Aykroyd, Fishers, IN (US); Alexander Licht, Weinheim (DE); Stephanie Ann Wooten, Tipton, IN (US)

(73) Assignee: Roche Diabetes Care, Inc., Indianapolis, IN (US)

( * ) Notice: Subject to any disclaimer, the term of this patent is extended or adjusted under 35 U.S.C. 154(b) by 493 days.

(21) Appl. No.: 18/353,937

(22) Filed: Jul. 18, 2023

(65) Prior Publication Data

US 2023/0355875 A1 Nov. 9, 2023

Related U.S. Application Data

(63) Continuation of application No. PCT/US2022/012708, filed on Jan. 18, 2022.
(Continued)

(51) Int. Cl.
*A61M 5/172* (2006.01)
*G16H 20/17* (2018.01)
*G16H 40/40* (2018.01)

(52) U.S. Cl.
CPC .......... *A61M 5/1723* (2013.01); *G16H 20/17* (2018.01); *G16H 40/40* (2018.01); *A61M 2205/50* (2013.01)

(58) Field of Classification Search
CPC ..... A61M 5/1723; G16H 20/17; G16H 40/63; A61B 5/02416
See application file for complete search history.

(56) References Cited

U.S. PATENT DOCUMENTS 5,884,620 A 3/1999 Gonda
8,948,832 B2 2/2015 Hong
(Continued)

FOREIGN PATENT DOCUMENTS

EP 2605698 4/2020
WO 2010025427 A1 3/2010
(Continued)

OTHER PUBLICATIONS

Nam, Yunyoung, et. al.; Photoplethysmography Signal Analysis for Optimal Region-of-Interest Determination in Video Imaging on a Built-In Smartphone under Different Conditions; journal "Sensors"; Oct. 19, 2017; pp. 1-18 at https: www.mdpi.com/1424/8220/17/10/2385.
(Continued)

*Primary Examiner* — Laura A Bouchelle
(74) *Attorney, Agent, or Firm* — Roche Diabetes Care, Inc.

(57) ABSTRACT

Medical device efficiency detection methods and systems including a photoplethysmography (PPG) sensor device, a processor, a memory, and machine readable instructions that may cause the system to receive a notification at the PPG device from the medical device upon delivery of the therapy treatment, use the PPG device to search for a signal response of the user based on the notification within a period of time to generate a response signal indicative of therapy treatment delivery, and transmit an alert when the response signal is not generated in the period of time indicative of a failure to detect sufficient therapy treatment delivery. The instructions may cause the system to transmit an alert when signal measurements from the PPG device of an infusion site are not within a sufficient signal range to indicate the infusion site is insufficient for delivery of the therapy treatment by the medical device.

20 Claims, 8 Drawing Sheets

Related U.S. Application Data

(60) Provisional application No. 63/138,945, filed on Jan. 19, 2021.

(56) References Cited

U.S. PATENT DOCUMENTS

| | | | |
|---|---|---|---|
| 9,320,851 B2 * | 4/2016 | Regittnig | A61M 5/16877 |
| 9,962,486 B2 | 5/2018 | Rosinko et al. | |
| 11,241,530 B1 * | 2/2022 | Fridez | A61M 5/1723 |
| 2008/0139900 A1 | 6/2008 | Randlov et al. | |
| 2013/0237955 A1 | 9/2013 | Neta | |
| 2013/0276785 A1 | 10/2013 | Melker et al. | |
| 2014/0058747 A1 | 2/2014 | Thompson et al. | |
| 2014/0276409 A1 | 9/2014 | Rosinko et al. | |
| 2017/0014572 A1 | 1/2017 | Newberry | |
| 2018/0055454 A1 * | 3/2018 | Newberry | A61B 5/7278 |
| 2018/0326147 A1 | 11/2018 | Sia | |
| 2019/0076601 A1 | 3/2019 | Newberry | |
| 2019/0328330 A1 | 10/2019 | Inan | |

FOREIGN PATENT DOCUMENTS

| | | | |
|---|---|---|---|
| WO | 2012024106 A2 | 2/2012 | |
| WO | 2018118256 A1 | 6/2018 | |
| WO | 2018136413 A2 | 7/2018 | |
| WO | 2019213493 A1 | 11/2019 | |
| WO | 2019237281 A1 | 12/2019 | |

OTHER PUBLICATIONS

International Search Report and Written Opinion; PCT/US2022/12708; Apr. 22, 2022; pp. 1-9.

* cited by examiner

270

Pulsatile arterial blood

Non pulsatile arterial blood

Venous blood

Tissue

NON-INVASIVE MEDICAL DEVICE EFFICIENCY AND FAULT DETECTION SYSTEMS AND METHODS OF USE

RELATED APPLICATIONS

This application is a continuation of PCT/2022/012708, filed on Jan. 18, 2022, which claims priority to U.S. Provisional Application No. 63/128,945, filed Jan. 19, 2021, both of which are incorporated herein by reference in their entirety.

TECHNICAL FIELD

The present specification generally relates to non-invasive medical device efficiency detection systems and methods of use and, more specifically, to non-invasive medical device efficiency and fault detection systems and methods of use to determine insulin fault detection, insulin site sufficiency, or combinations thereof using closed loop connected devices.

BACKGROUND

A medical device may be used to administer therapies to treat a disease, such as delivery of insulin via an insulin dosing to diabetic users. At times the medical device may include a fault such as an occlusion which prevents delivery of the insulin but may be undetected. The medical device may further deliver the therapies at sites at which optimal amounts of insulin are not administered.

Accordingly, a need exists for alternative systems to efficiently deliver therapies to treat users via a medical device system and methods of use of such systems.

SUMMARY

In one embodiment, a medical device efficiency detection system may include a photoplethysmography (PPG) sensor device, a medical device configured to administer a therapy treatment, a processor communicatively coupled to the PPG sensor device and the medical device, a memory communicatively coupled to the processor, and machine readable instructions stored in the memory. The machine readable instructions may cause the medical device efficiency detection system to perform at least the following when executed by the processor: communicatively connect the PPG sensor device and the medical device, deliver the therapy treatment to a user at an infusion site through the medical device, receive a notification at the PPG sensor device from the medical device upon delivery of the therapy treatment, use the PPG sensor device to search for a signal response of the user based on the notification within a period of time to generate a response signal indicative of therapy treatment delivery, and transmit an alert when the response signal is not generated in the period of time indicative of a failure to detect sufficient therapy treatment delivery.

In one other embodiment, a medical device efficiency detection system may include a photoplethysmography (PPG) sensor device, a medical device configured to administer a therapy treatment, a processor communicatively coupled to the PPG sensor device and the medical device, a memory communicatively coupled to the processor, and machine readable instructions stored in the memory. The machine readable instructions may cause the medical device efficiency detection system to perform at least the following when executed by the processor: communicatively connect the PPG sensor device and the medical device, deliver the therapy treatment to a user at an infusion site through the medical device, receive a notification at the PPG sensor device from the medical device upon delivery of the therapy treatment, use the PPG sensor device to search for a signal response of the user based on the notification within a period of time to generate a response signal indicative of therapy treatment delivery, and transmit an alert when the response signal is not generated in the period of time indicative of a failure to detect sufficient therapy treatment delivery, when the response signal is generated after a delay period in the period of time, when the response signal generated in the period of time is under a threshold value, or combinations thereof.

In yet one other embodiment, a medical device efficiency detection system may include a photoplethysmography (PPG) sensor device, a processor communicatively coupled to the PPG sensor device, a memory communicatively coupled to the processor, and machine readable instructions stored in the memory. The machine readable instructions may cause the medical device efficiency detection system to perform at least the following when executed by the processor: dispose the PPG sensor device over an infusion site of a user at which a medical device is to administer a therapy treatment, generate signal measurements from the PPG sensor device with respect to tissue and vasculature underlying the infusion site, determine whether the signal measurements are within a sufficient signal range such that the infusion site is sufficient for delivery of the therapy treatment by the medical device, and transmit an alert when the signal measurements are not within the sufficient signal range to indicate the infusion site is insufficient for delivery of the therapy treatment by the medical device.

These and additional features provided by the embodiments described herein will be more fully understood in view of the following detailed description, in conjunction with the drawings.

BRIEF DESCRIPTION OF THE DRAWINGS

The embodiments set forth in the drawings are illustrative and exemplary in nature and not intended to limit the subject matter defined by the claims. The following detailed description of the illustrative embodiments can be understood when read in conjunction with the following drawings, where like structure is indicated with like reference numerals and in which:

DETAILED DESCRIPTION

Figure 1:
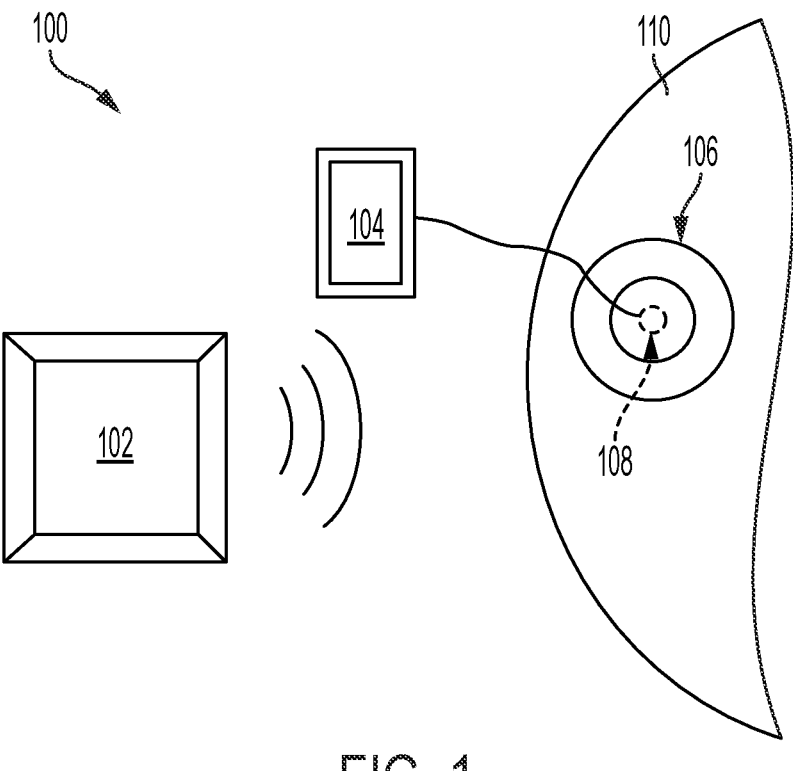
FIG. 1 schematically illustrates a medical device efficiency detection system including a photoplethysmography (PPG) sensor device and an insulin delivery device to deliver insulin to a user at an infusion site, according to one or more embodiments shown and described herein.

Referring generally to the figures, embodiments of the present disclosure are directed to medical device efficiency detection systems to detect fault (such as occlusions of delivery devices) or insufficient or otherwise ineffective treatment delivery and methods of use of such closed loop systems to prevent, for example, a potential hyperglycemic state of a diabetic user. Closed loop systems may reference systems including a continuous glucose monitor and an insulin delivery device such as an insulin pump to automatically regulate insulin of a user with minimal user interaction to act as an artificial pancreas. Open loop systems may references systems that combine external insulin pumps with real-time continuous glucose monitoring via subcutaneous sensors that communicate glucose readings to the external insulin pumps. It is within the scope of this disclosure that the systems described herein may be utilized with closed loop and/or open loop systems for diabetes management. Reference will now be made in detail to embodiments of the medical device efficiency detection systems, and examples of such systems are illustrated in the accompanying drawings. Wherever possible, the same reference numerals will be used throughout the drawings to refer to the same or like parts. Various embodiments of the medical device efficiency detection systems will be described in further detail herein with specific reference to the appended drawings.

Referring to FIG. 1, a medical device efficiency detection system 100 is shown including a photoplethysmography (PPG) sensor device 102 and a medical device 104 to deliver a treatment therapy at an infusion site 108 to a user 110. In an embodiment, the medical device 104 may be an insulin delivery device, and the treatment therapy may be a dosing of insulin. The insulin delivery device may include and be coupled to a cradle 106 attached to the user 110 at the infusion site 108. The PPG sensor device 102 may be a separate wearable device, separate from the medical device 104, and configured to be disposed at an area on the user 110 remove from the infusion site 108 and the medical device 104. The PPG sensor device 102 may be a wristband, a ring, a fingerclip, an adhesive patch, a toe clip, ear buds, earrings, or a forehead band, or other suitable wearable device. Alternatively, the PPG sensor device 102 may be a mobile smart device. A camera and flash of the mobile smart device may be configured to act as a photodiode and light source of the PPG sensor device 102 respectively.

In other embodiments, the PPG sensor device 102 may be integrated with the medical device. As a non-limiting example, the PPG sensor device 102 may be incorporated into the medical device 104, which may be an insulin pump adhered to the skin of the user 110. For a patch pump, the PPG sensor device 102 may be integrated within the cradle 106 set against the body of the user 110 at the infusion site 108. Alternatively, the PPG sensor device 102 may be placed within the medical device 104, such as in an infusion set. In embodiments, the PPG sensor device 102 may communicate via a communicatively coupling with the medical device 104 associated with an insulin delivery device, such as an insulin pump, an insulin pen, an insulin inhaler, or a dedicated controller for an insulin delivery device. When glucose information is monitored for insulin fault detection by the medical device 104 as a glucose monitoring device, the PPG sensor device 102 may also be directly or indirectly connected and communicatively coupled to the glucose monitoring device.

In various embodiments, the medical device efficiency detection system 100 may operate the PPG sensor device 102 to use PPG signals to assist in efficient insulin dosing for diabetic patients. The medical device efficiency detection system 100 may determine when insulin is delivered via the medical device 104 (such as via an insulin pump, insulin pen, or insulin inhaler), and may use the PPG sensor device 102 to detect a physiological responses of the user to the presence of the delivered insulin upon notification of delivery by the medical device 104. The PPG sensor device 102 may be used to determine if and when insulin is being absorbed by the body due to a physiological response. When a user doses insulin, if the physiological response is not measured, the user can be alerted before a potentially dangerous situation occurs to prevent a potential hyperglycemic state.

The medical device 104 may be configured to administer a therapy treatment such as inulin delivery through insulin dosing of the user 110. Such insulin dosing may be a prescribed method for the user 110 to manage glucose for diabetics. The insulin may be dosed to the user via several types of medical device 104 forms, such as insulin pumps, insulin pens, inhaled insulin, and/or traditional shots. Such medical device 104 forms may have an issue with occlusions/impediments that may reduce an efficiency of insulin delivery by the medical device 104 to the user 110. For example, a cannula associated with the medical device 104 to deliver insulin to the user 110 may become occluded such that the insulin issued by the medical device 104 is not delivered to the user 110 due to a downstream occlusion. An upstream occlusion may also occur between an insulin reservoir and the insulin pump if, for example, the reservoir is running low. Leakages within the insulin pump or near the infusion site 108 may also occur and result in disruptions to the insulin delivery to the user 110 and reduced effectiveness of such insulin delivery via the medical device 104.

In embodiment configurations, the PPG sensor device 102 could be a secondary insulin fault detection mechanism for the medical device 104 that may be an insulin pump already containing internal fault detection sensors. Such internal fault detection sensors may include sensors integrated within an insulin pump device, for example, either near the reservoir, the pump motor or downstream into the tubing and cannula, to measure various forces, volume, pressure, and optical changes within the insulin pump device system that may indicate an occlusion. However, such internal fault detections sensors may not detect the occlusion and issue an alarm until hours after the occlusion occurs, which may result in the user 110 entering a dangerous hyperglycemic state with little warning to intervene. The PPG sensor device 102 described herein may be used to verify or confirm faults detected internally within the insulin pump, or to identify an anomaly before a fault is detected within the insulin pump by the internal fault detection sensors, and to notify the user 110 via a pump controller interface to check pump functionality and monitor user blood glucose (bg) levels closely for a possible impending occlusion alarm from the insulin pump.

The PPG sensor device 102 operates to sense insulin absorption to the user 110 via the medical device 104 through sensing a resulting physiological response of the user 110 to the delivered insulin. For example, as insulin is delivered to the body, a body of the user reacts with a physiological response of their vasculature of vasoconstriction or vasodilation, which changes the volumetric blood flow through the body. In particular, when insulin is released into the body, the body subsequently produces nitric oxide (NO) and/or Endothelin (ET-1) compounds. These compounds cause the arteries of the vasculature to expand or contract, which respectively allows for a higher or lower volumetric blood flow. PPG is an optical sensing technology used to monitor heart rate and heart rate variability that is capable of measuring the changes in volumetric blood flow. The PPG process involves using shining a light, such as from a LED, in one or more different wavelengths, to in turn measure the amount of light that is reflected or transmitted to a photodiode. Volumetric changes in blood flow cause the change in the amount of light that is measured by the photodiode. Such a change in volumetric blood flow is represented in a PPG signal, such as at specific frequencies of light between 375 and 550 nm wavelengths, though measurements at other frequencies are possible.

In embodiments in which the medical device 104 is an insulin pump, insulin absorption for the user 110 may vary over time and an infusion set wear time at an infusion site 108 may be limited to 1-3 days before the infusion site 108 has to be changed depending on a type of cannula and other local factors. The medical device efficiency detection system 100 may operate to determine if and when an infusion site 108 needs to be changed. The medical device efficiency detection system 100 may thus operate to inform the user 110 about an infusion set wear time associated with an infusion site 108 to most efficiently user the infusion site 108. By advising the user of the infusion set wear time, a well-functioning set will be prevented from being disposed of prematurely, and further will not be worn too long where such that the set may no longer be optimally performing associated insulin delivery functions.

Further, tissue damage, bruising, local infection, and/or lipohypertrophy (increased localized fat cells) may develop as a result of repeated and long term insulin pump/infusion set usage with poor site rotation. Anatomical and physiological changes that present at these 'over-used' sites may result in reduced and less effective insulin absorption and ultimately unexpected abnormal glycemic outcomes. Moreover, some sites that are not optimal for infusion placement may include areas where there is known scar tissue, a previous surgical scar, stretch marks, fatty tissue overgrowth, previously infected areas, bruised areas, or areas which have previously undergone liposuction, and the other similar sites with characteristics that reduce efficiency of insulin absorption.

While user may change infusion sets every 1-3 days, they may also be instructed to not use the same infusion site 108 within for at least two weeks until the infusion site 108 has fully healed. Further, once a cannula of the medical device 104 has been inserted as an infusion set in one infusion site 108, a user 110 is usually advised not remove it and replace the same infusion set in another infusion site 108 due to risk of infection. A user 110 may use an infusion site rotation pattern to avoid re-using the same site prior to the site being healed, such that the user 110 may move the infusion site 108 progressively along a certain path (e.g. horizontal, zigzag, curve, crisscross). However, such movement does not ensure the next site along the pattern will be optimal for insulin delivery, and the user 110 may make a tracking error that can cause an unreliable or otherwise inefficient site to be used. The medical device efficiency detection system 100 may operate to manage where past infusion sites 108 for a user 110 have been and to avoid new areas that may not optimally absorb insulin. The medical device efficiency detection system 100 as described herein may further operate to effectively identify efficient and suitable locations for infusion set placement to maintain consistent and predictable insulin delivery for optimal diabetes management and reduce costs associated with poor placement and wasted infusion sets that may have to be prematurely discarded due to local site issues.

Thus, the PPG sensor device 102 may further be used as described in greater detail below to determine when it is time to change an infusion site 108 due to decrease in insulin absorption and more effectively deliver insulin to a user at a new infusion site 108. Moreover, as will be described in greater detail further below, the medical device efficiency detection system 100 may be used to scan a potential insulin infusion site 108 to determine suitability to place an insulin infusion set such as the medical device 104. The medical device efficiency detection system 100 may use the PPG sensor device 102 as described herein to determine if insulin is successfully and efficient delivered to the user 110 to treat diabetes and to determine when insulin is delivered upon detection of a physiological responses to the presence of insulin in response to a notification of insulin delivery by the medical device 104. When the user 110 doses insulin via the medical device 104, and if the physiological response is not measured by the PPG sensor device 102 upon notification of the delivery and within a period of time after the notification and delivery, the user 110 can be alerted before a potentially dangerous situation occurs, which may prevent a potential hyperglycemic state. The medical device efficiency detection system 100 may further monitor infusion site wear time and optimally identify new infusion sites 108 using PPG signals from the PPG sensor device 102 as described in greater detail below with respect to the process 600 of FIG. 8.

Figure 2:
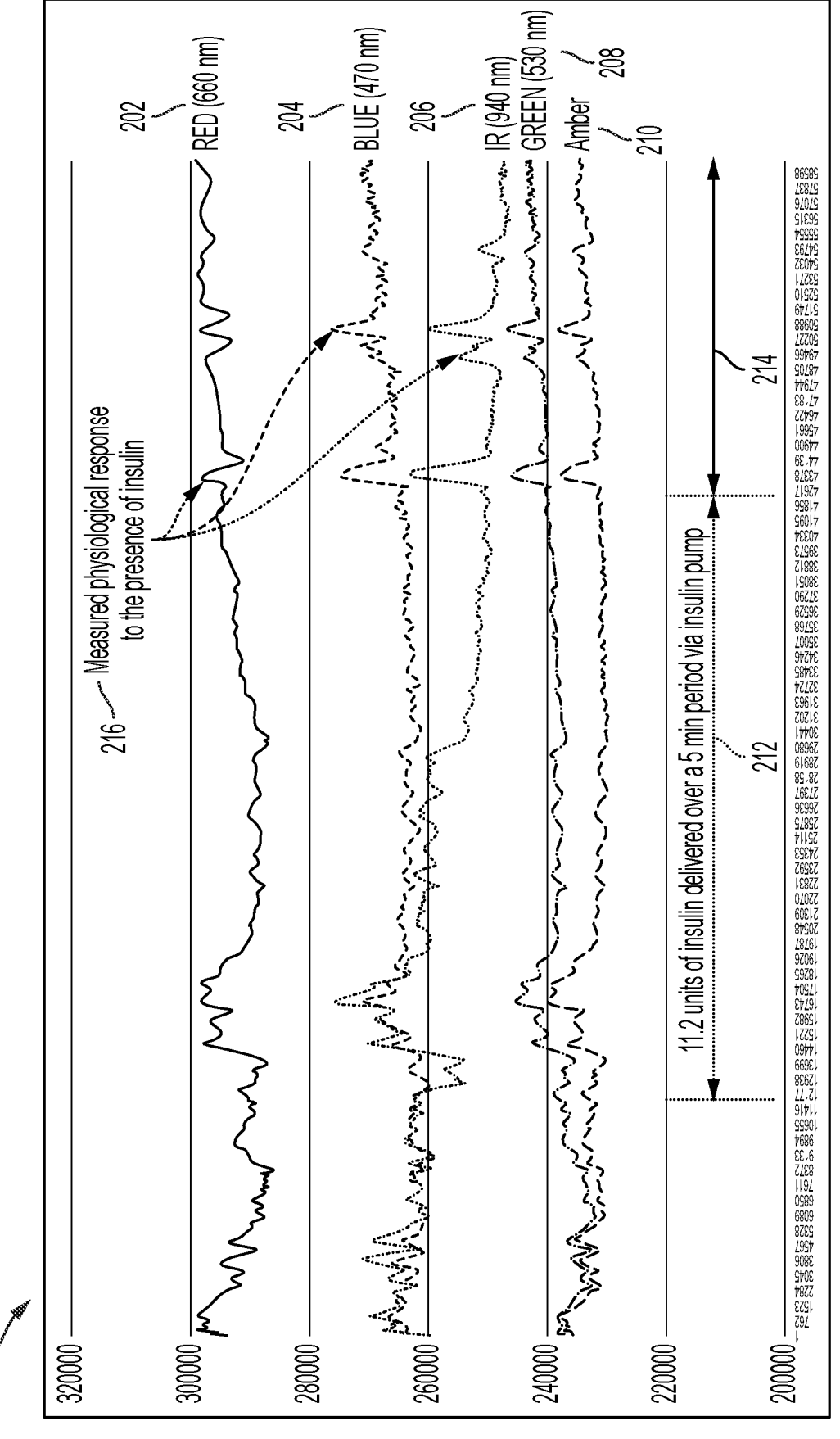
FIG. 2 schematically illustrates a measured physiological response to the presence of insulin delivered by the insulin delivery device of FIG. 1 as detected by the PPG sensor device at different wavelengths.

Referring to FIG. 2, a profile 200 is shown of a measured physiological response to the presence of insulin delivered to a user by the insulin delivery device as the medical device 104 of FIG. 1 as detected by the PPG sensor device 102 at different wavelengths. With respect to FIG. 2, the medical device 104 is an insulin pump worn by the user delivering insulin at a basal rate of 1.15 units per hour, and one bolus of insulin is administered over a 10 minute test time. The applied wavelengths are red 202 at 660 nm, blue 204 at 470 nm, infrared (IR) 206 at 940 nm, green 208 at 530 nm, and amber 210. While the wavelengths are shown in FIG. 2 at certain wavelengths with different frequencies, it is contemplated by and within the scope of this disclosure that different wavelengths than those of FIG. 2 may be utilized by the PPG sensor device 102. As a non-limiting example, the PPG sensor device 102 may transmit light toward the user 110 of one or more different colors along a light spectrum and having wavelengths in a range of between 380 nm to 1200 nm and measure a corresponding light reflected back to a transducer component of the PPG sensor device 102, such as a photodiode, to measure an absorption amount related to the transmitted and reflected light. In at least one other embodiment, PPG sensor device may transmit light toward the user 110 of one or more different colors along a light spectrum and having wavelengths in a range of between 380 nm to 1200 nm and measure a corresponding light transmitted through a portion of the body to a transducer component of the PPG sensor device 102, such as a photodiode, to measure an absorption amount related to the transmissive light. Examples of this transmissive embodiment may occur at sites such as the ear lobe or finger tip. The x-axis of FIG. 2 represents unit of time, and the y-axis represents absorption for the applied wavelengths of the user vasculature as detected by PPG sensor device 102.

Figure 4:
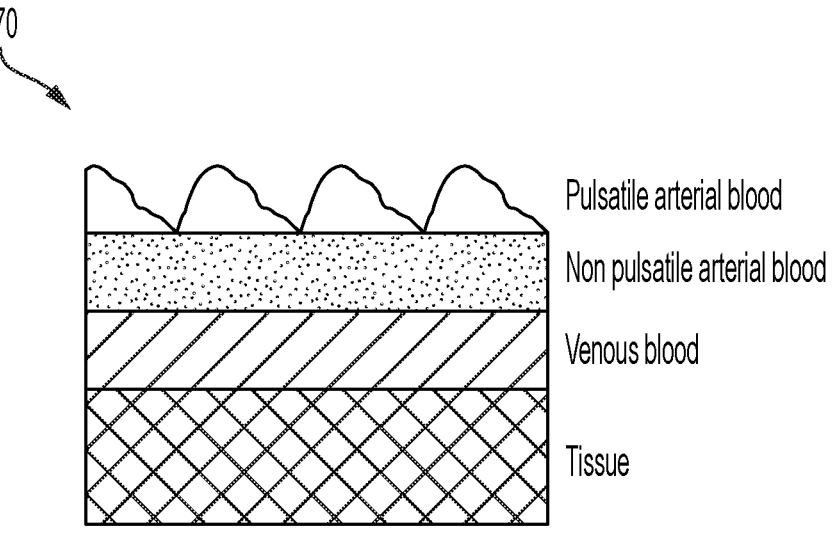
FIG. 4 is a schematic diagram representative of PPG sensor device signals corresponding to underlying tissue and vasculature, according to one or more embodiments shown and described herein.

The PPG sensor device 102 is configured to be used as a non-invasive pulse oximeter device to measure oxygen saturation and light absorption of blood. As a pulse oximeter, the PPG sensor device 102 uses spectrophotometry to determine spectral absorption of different transmitted light wavelengths corresponding to different colors on the light spectrum, determine oxygen concentration levels through such measurements, and utilize PPG methods to assess oxygen saturation in a pulsatile arterial blood flow of vasculature to which the light is transmitted. To measure oxygen saturation of the arterial blood, the PPG sensor device 102 may filter an absorbance of a pulsatile fraction of the blood due to arterial blood as an AC component from a constant absorbance of the blood by non-pulsatile components as DC Hcomponents, as shown in FIG. 4 described in further detail below. When insulin is delivered to the vasculature, a vasculature dilation may occur followed by a vasoconstriction such that more light is absorbed to indicate the absorption of insulin in the vasculature for a period of time prior to having more light reflected back. When more light is absorbed, less light is reflected back to the PPG sensor device 102. The PPG sensor device 102 may compare this light absorption measurement to a baseline measurement without insulin delivery, such as a baseline vasoconstriction of a vascular system for the user 110 or a baseline NO value for the user 110. When the light absorption measurement is above the baseline measurement, the PPG sensor device 102 may determine that insulin has been absorbed by measured vasculature of and thus been delivered to the user 110.

Figure 3:
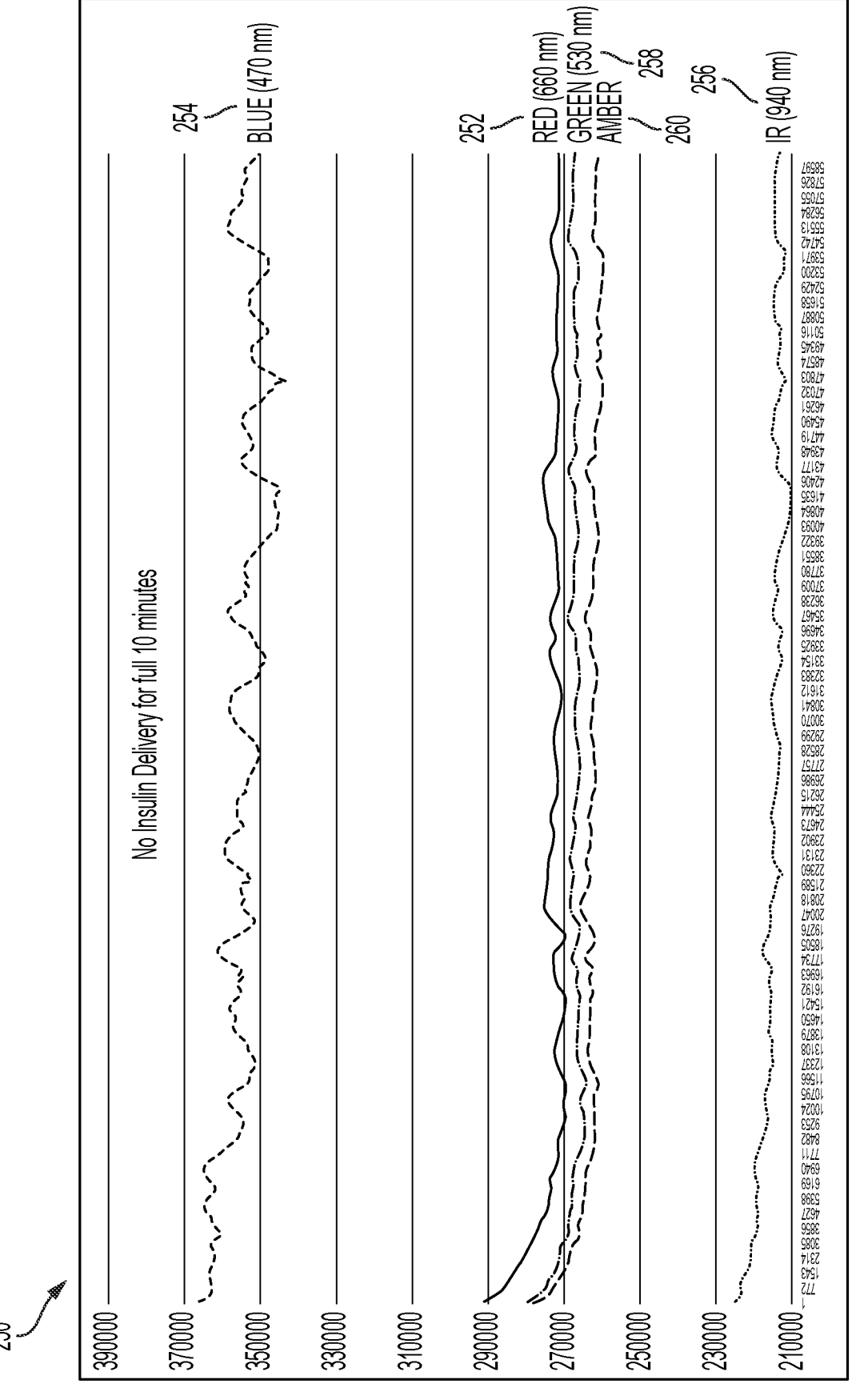
FIG. 3 schematically illustrates a measured physiological response as detected by the PPG sensor device of FIG. 1 at different wavelengths when insulin has not been delivered.

Referring to FIG. 2, a period 212 reflects a delivery of 11.2 units of insulin to the user over a 5 minute period using the insulin pump, and a period 214 reflects a period thereafter when the PPG sensor device 102 detects one or more measured physiological responses to the presence of insulin as one or more respective peaks 216. For example, during an insulin delivery event, a spike in the raw PPG data or a necking feature in PPG data with the DC removed and normalized can be seen as the one or more respective peaks 216. In contrast, referring to FIG. 3, a profile 250 is shown of a measured physiological response over a 10 minute time period as detected by the PPG sensor device 102 of FIG. 1 at different wavelengths when insulin has not been delivered to the user by the medical device 104. Detection of insulin delivery in at least one embodiment involves the identification of peaks 216 in at least one wavelength examined. In an addition embodiment, peaks are identified in at least two wavelengths examined to indicate insulin delivery. In an addition embodiment, peaks are identified in at least three wavelengths examined to indicate insulin delivery. In an addition embodiment, peaks are identified in at least four wavelengths examined to indicate insulin delivery. In an addition embodiment, peaks are identified in at least five wavelengths examined to indicate insulin delivery.

Referring again to FIG. 2, each peak 216 may be determined based on a difference between two points within a timeframe over a threshold value to indicate the presence of insulin. As a non-limiting example, two points within a 15 second timeframe have a difference that is more than a 2% increase may overcome a threshold value of a positive 2% change to indicate the presence of insulin. In other embodiments, the threshold value may be of a positive slope change between two points that is a slope change of over 3 times, and the period timeframe within which the two points are disposed may be within a range of 10 seconds to 40 seconds. Alternately, in other embodiments, the threshold value may if a calculated value, such as the area under a curve, over a set threshold of time is present. Additionally, the pulse width of the signal may be used to indicate the threshold value.

In embodiments, the PPG sensor device 102 may thus be placed in a closed loop communication with the medical device 104, such as an insulin delivery device. A communication between the devices may be used to provide a notification indicate when basal or bolus insulin is delivered by the medical device 104. Upon receipt of the notification of delivery, the connected PPG sensor device 102 may then be used to monitor for a period of time for raw or filtered spectral signatures correlated with insulin activity in the body of the user 110 in response to the insulin delivery. In embodiments, as shown in FIG. 2, such specific signature may include a sharp rise in the raw PPG signal similar to a DC shift. When the signal is normalized and filtered to remove the DC portion, a constriction or necking of the signal may result. Such a specific signature to indicate insulin absorption in the user 110 may occur instantaneously or up to approximately 5 minutes after insulin delivery. If no such signature is seen within a certain time threshold after the notification of delivery, an alert may be sent to the user alerting them to the situation before a dangerous health condition is experienced. Further, the user 110 may be notified to monitor their blood glucose levels via a self-monitoring blood glucose device or a continuous glucose monitor to look for increasing glucose levels and trends.

For example, there are distinct patterns in the PPG saw tooth waveform to describe a physiological response from the presence of vasodilators and vasoconstrictors as a result of insulin dosing as shown in FIG. 2. For a raw PPG signal after a bandpass or notch filter has removed noise, a dosage or release of insulin may cause a gradual increase of the DC signal, which eventually returns back to the normal DC baseline after approximately 10-40 seconds. Additionally, when comparing peaks for different wavelengths of light of the sawtooth waveform for a same cardiac stroke, time differences between the peak height may be affected. For example, by comparing a PPG signal from red light to a PPG signal for UV light, the peak for red light could be reached at $T_{red}$ and the peak for UV light could be reached at $T_{UV}$. A difference or delta between $T_{red}$ and $T_{UV}$ may vary as a result of insulin being dosed (e.g., released) into the user 110. Further, R values such as those used for the calculation of pulse oximetry may be affected as well, where such R values may be used to compare the AC and DC portions of one wavelength of light to another to detect insulin absorption.

For a PPG signal which has the DC portion of the signal removed, the PPG signal may exhibit lower amplitude or peak heights for a time period of approximately 10-40 seconds after the dosage/release of insulin. Further, the time difference between peak heights for different wavelengths of light could also be impacted.

As PPG signals are susceptible to noise, the PPG signal could experience a DC shift as a result of motion. Thus, the medical device efficiency detection system 100 may operate in a closed loop communication and be configured to indicate when a bolus is delivered by the medical device 104 and when the DC shift is detected by the PPG sensor device 102 within a period of time after the delivery to verify a DC shift is indicative of insulin delivery rather than motion.

Further, on-board accelerometers may be used to determine whether excessive motion is contributing to the DC shift after an insulin dosing event. Other factors causing noise to the PPG signal of the PPG sensor device 102 may include ambient light conditions, temperature, amount of pressure applied to the sensor surface, respiratory rate, level of perspiration between skin and the device, or variable heart rate. The medical device efficiency detection system 100 may be configured to filter the PPG signal with an applied filter to reduce such noise.

FIG. 4 shows a diagram 270 of example PPG sensor device signals from the PPG sensor device 102 that may correspond to underlying tissue and vasculature. For instance, as described in greater detail below with respect to FIG. 8, the PPG sensor device 102 may be used to check an infusion site to determine whether it is sufficient to use to efficiently deliver insulin. In the diagram 270, tissue, venous blood, and non-pulsatile arterial blood are representative of DC components of respective PPG signals received by the PPG sensor device 102, and pulsatile arterial blood is representative of an AC component of a PPG signal received to indicate pulsation via contraction and expansion of the underlying blood vessel. Hence, if the PPG signal for the pulsatile arterial blood at a tested infusion site does not provide a sufficient amplitude or appropriate AC component, the medical device efficiency detection system 100 may determine the tested infusion site is not sufficient for use to deliver insulin (e.g., not including underlying vasculature sufficient for insulin absorption) compared to another infusion site that may be similarly tested for sufficiency.

Figure 5:
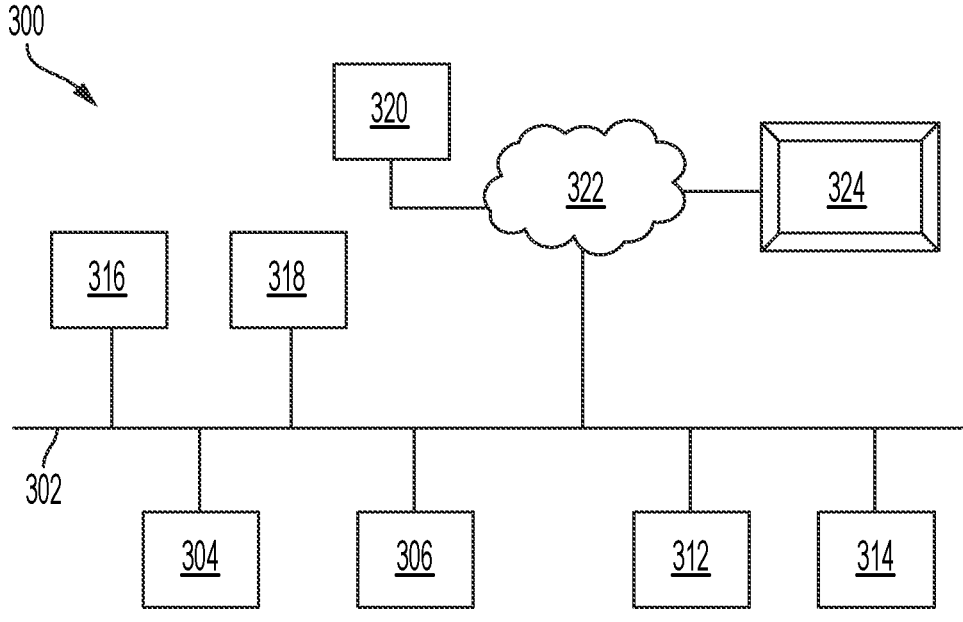
FIG. 5 schematically illustrates a system for implementing computer and software based methods to utilize the medical device efficiency detection system of FIG. 1, according to one or more embodiments shown and described herein.

Referring to FIG. 5, a system 300 for implementing a computer and software-based method to utilize the medical device efficiency detection system, as shown in FIG. 1, is illustrated and may be implemented along with using a graphical user interface (GUI) that is accessible at a user workstation (e.g., a computer 324), for example. The system 300 includes a communication path 302, one or more processors 304, a memory component 306 (e.g., memory 306), a PPG sensing component 312, a storage or database 314, a treatment delivery component 316, a network interface hardware 318, a server 320, a network 322, and at least one computer 324. The various components of the system 300 and the interaction thereof will be described in detail below.

While only one application server 320 and one user workstation computer 324 is illustrated, the system 300 can include multiple workstations and application servers containing one or more applications that can be located at geographically diverse locations across a plurality of industrial sites. In some embodiments, the system 300 is implemented using a wide area network (WAN) or network 322, such as an intranet or the Internet, or other wired or wireless communication network that may include a cloud computing-based network configuration (for example, the cloud). The workstation computer 324 may include digital systems and other devices permitting connection to and navigation of the network. Other system 300 variations allowing for communication between various geographically diverse components are possible. The lines depicted in FIG. 5 indicate communication rather than physical connections between the various components.

As noted above, the system 300 includes the communication path 302. The communication path 302 may be formed from any medium that is capable of transmitting a signal such as, for example, conductive wires, conductive traces, optical waveguides, or the like, or from a combination of mediums capable of transmitting signals. The communication path 302 communicatively couples the various components of the system 300. As used herein, the term "communicatively coupled" means that coupled components are capable of exchanging data signals with one another such as, for example, electrical signals via conductive medium, electromagnetic signals via air, optical signals via optical waveguides, and the like.

As noted above, the system 300 includes the processor 304. The processor 304 can be any device capable of executing machine readable instructions. Accordingly, the processor 304 may be a controller, an integrated circuit, a microchip, a computer, or any other computing device. The processor 304 is communicatively coupled to the other components of the system 300 by the communication path 302. Accordingly, the communication path 302 may communicatively couple any number of processors with one another, and allow the modules coupled to the communication path 302 to operate in a distributed computing environment. Specifically, each of the modules can operate as a node that may send and/or receive data. The processor 304 may process the input signals received from the system modules and/or extract information from such signals.

As noted above, the system 300 includes the memory component 306 which is coupled to the communication path 302 and communicatively coupled to the processor 304. The memory component 306 may be a non-transitory computer readable medium or non-transitory computer readable memory and may be configured as a nonvolatile computer readable medium. The memory component 306 may comprise RAM, ROM, flash memories, hard drives, or any device capable of storing machine readable instructions such that the machine readable instructions can be accessed and executed by the processor 304. The machine readable instructions may comprise logic or algorithm(s) written in any programming language such as, for example, machine language that may be directly executed by the processor, or assembly language, object-oriented programming (OOP), scripting languages, microcode, etc., that may be compiled or assembled into machine readable instructions and stored on the memory component 306. Alternatively, the machine readable instructions may be written in a hardware description language (HDL), such as logic implemented via either a field-programmable gate array (FPGA) configuration or an application-specific integrated circuit (ASIC), or their equivalents. Accordingly, the methods described herein may be implemented in any conventional computer programming language, as pre-programmed hardware elements, or as a combination of hardware and software components. In embodiments, the system 300 may include the processor 304 communicatively coupled to the memory component 306 that stores instructions that, when executed by the processor 304, cause the processor to perform one or more functions as described herein.

Still referring to FIG. 5, as noted above, the system 300 comprises the display such as a GUI on a screen of the computer 324 for providing visual output such as, for example, information, graphical reports, messages, or a combination thereof. The computer 324 may include one or more computing devices across platforms, or may be communicatively coupled to devices across platforms, such as mobile smart devices including smartphones, tablets, laptops, and/or the like or medical devices such as blood glucose meters, insulin pumps, continuous glucose monitors, and the like. The display on the screen of the computer 324 is coupled to the communication path 302 and communicatively coupled to the processor 304. Accordingly, the communication path 302 communicatively couples the display to other modules of the system 300. The display can include any medium capable of transmitting an optical output such as, for example, a cathode ray tube, light emitting diodes, a liquid crystal display, a plasma display, or the like. Additionally, it is noted that the display or the computer 324 can include at least one of the processor 304 and the memory component 306. While the system 300 is illustrated as a single, integrated system in FIG. 5, in other embodiments, the systems can be independent systems.

The system 300 comprises the PPG sensing component 312, such as the PPG sensor device 102 described herein, and the treatment delivery component 316, such as the medical device 104 configured to administer a treatment therapy as described herein. The PPG sensing component 312 and the treatment delivery component 316 are coupled to the communication path 302 and communicatively coupled to the processor 304. As will be described in further detail below, the processor 304 may process the input signals received from the system modules and/or extract information from such signals.

The system 300 includes the network interface hardware 318 for communicatively coupling the system 300 with a computer network such as network 322. The network interface hardware 318 is coupled to the communication path 302 such that the communication path 302 communicatively couples the network interface hardware 218 to other modules of the system 300. The network interface hardware 318 can be any device capable of transmitting and/or receiving data via a wireless network. Accordingly, the network interface hardware 318 can include a communication transceiver for sending and/or receiving data according to any wireless communication standard. For example, the network interface hardware 318 can include a chipset (e.g., antenna, processors, machine readable instructions, etc.) to communicate over wired and/or wireless computer networks such as, for example, wireless fidelity (Wi-Fi), WiMax, Bluetooth, IrDA, Wireless USB, Z-Wave, ZigBee, or the like.

Still referring to FIG. 5, data from various applications running on computer 324 can be provided from the computer 324 to the system 300 via the network interface hardware 318. The computer 324 can be any device having hardware (e.g., chipsets, processors, memory, etc.) for communicatively coupling with the network interface hardware 318 and a network 322. Specifically, the computer 324 can include an input device having an antenna for communicating over one or more of the wireless computer networks described above.

The network 322 can include any wired and/or wireless network such as, for example, wide area networks, metropolitan area networks, the Internet, an Intranet, the cloud 323, satellite networks, or the like. Accordingly, the network 322 can be utilized as a wireless access point by the computer 324 to access one or more servers (e.g., a server 320). The server 320 and any additional servers such as a cloud server generally include processors, memory, and chipset for delivering resources via the network 322. Resources can include providing, for example, processing, storage, software, and information from the server 320 to the system 300 via the network 322. Additionally, it is noted that the server 320 and any additional servers can share resources with one another over the network 322 such as, for example, via the wired portion of the network, the wireless portion of the network, or combinations thereof.

Figure 6:
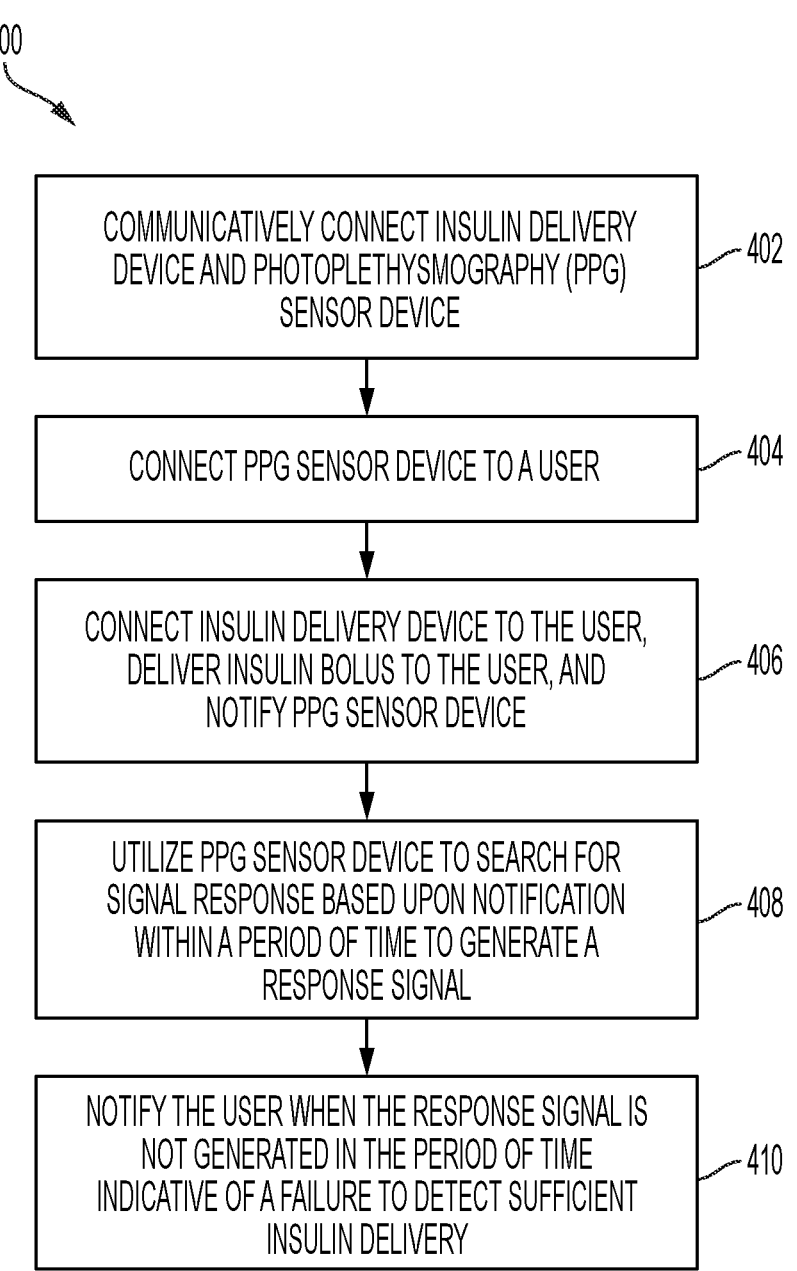
FIG. 6 is a flow chart of a process for using the systems of FIGS. 1 and 5, according to one or more embodiments shown and described herein.
Figure 7:
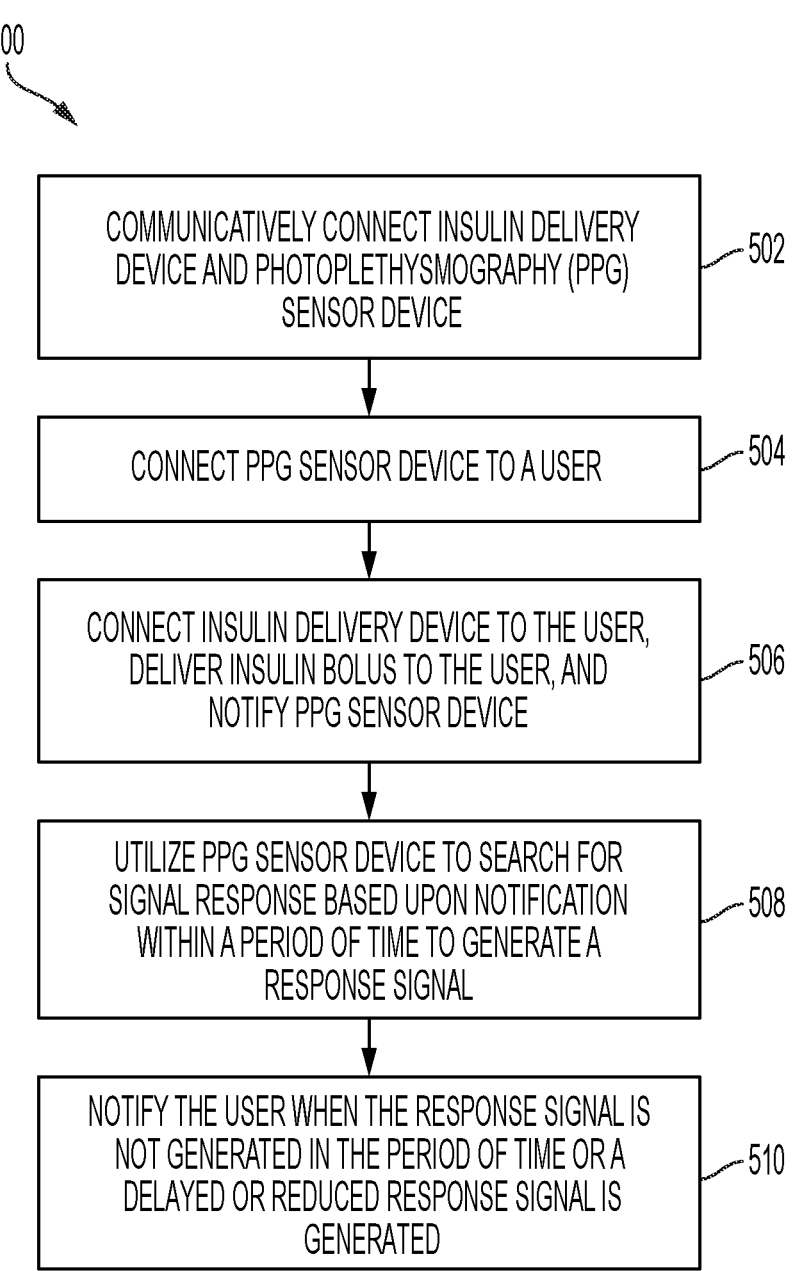
FIG. 7 is a flow chart of another process for using the systems of FIGS. 1 and 5, according to one or more embodiments shown and described herein.

Referring to FIGS. 6-7, respective processes 400, 500 are shown for using the medical device efficiency detection system 100 of FIG. 1 with the system 300 of FIG. 5, which implements the processes 400, 500 as described herein. In embodiments, the medical device efficiency detection system 100 includes the PPG sensor device 102, the medical device 104 configured to administer a therapy treatment, a processor 304 communicatively coupled to the PPG sensor device and the medical device, a memory 306 communicatively coupled to the processor 304, and machine readable instructions stored in the memory 306. The machine readable instructions may cause the medical device efficiency detection system 100 to perform the processes 400, 500 when executed by the processor 304.

With respect to the process 400, in block 402, the PPG sensor device 102 is communicatively coupled to the medical device 104. In block 404, the PPG sensor device 102 may be connected to the user 110.

In block 406, the medical device 104 may be an insulin delivery device connected to the user 110, and an insulin bolus may be delivered to the use via the medical device 104. Upon delivery of the insulin bolus, the medical device 104 may send a notification of the delivery to the PPG sensor device 102. Thus, in block 406, the system 300 may be configured to deliver the therapy treatment to the user at the infusion site 108 through the medical device 104 and receive a notification at the PPG sensor device 102 from the medical device 104 upon delivery of the therapy treatment.

In block 408, the PPG sensor device 102 may be used to search for a signal response in the user 110 based on the received notification and within a period of time to generate a response signal indicative of insulin absorption. Thus, in block 406, the system 300 may be configured to use the PPG sensor device 102 to search for the signal response of the user 110 based on the notification of delivery transmitted by the medical device 104 and within a period of time to generate the response signal indicative of therapy treatment delivery by the medical device 104.

In block 410, the user 110 may be notified when the response signal indicative of insulin absorption is not generated in the period of time such that the user 110 is notified of a failure by the PPG sensor device 102 to detect sufficient insulin delivery to the user 110 by the medical device 104. In embodiments, the system 300 may be configured to transmit an alert when the response signal indicative of therapy treatment delivery is not generated in the period of time indicative of a failure to detect sufficient therapy treatment delivery.

In embodiments, the system 300 may further be configured to transmit the alert when the response signal is generated after a delay period in the period of time. Additionally or alternatively, the system 300 may be configured to transmit the alert when the response signal generated in the period of time is under a threshold value. When the response signal generated is under the threshold value, the alert may include an indication to move the infusion site 108 to another location on the user 110.

With respect to the process 500, process steps 502-508 correspond to process steps 402-408 of the process 400. In block 510, however, the process 500 differs from the process 400 in that the user 110 may be notified not only when the response signal indicative of insulin absorption is not generated in the period of time, but also when a delayed or reduced response signal is generated by the PPG sensor device 102 indicative of a failure to detect sufficient insulin delivery. Thus, the user 110 is notified of a failure by the PPG sensor device 102 to detect sufficient insulin delivery to the user 110, either through no detection or a reduced (e.g., under an acceptable threshold indicative of sufficient insulin absorption) or delayed detection, by the medical device 104. In embodiments, the system 300 may be configured to transmit an alert when the response signal is not generated by the PPG sensor device 102 in the period of time indicative of a failure to detect sufficient therapy treatment delivery, when the response signal is generated after a delay period in the period of time, when the response signal generated in the period of time is under a threshold value, or combinations thereof.

Accordingly, the PPG sensor device 102 may act as a mechanism to alert the user 110 when it is time to change an infusion site 108. Thus, an associated infusion set wear time at the infusion site 108 may be personalized to the user 110 based on an effectiveness of the insulin being absorbed over time as monitored by the PPG sensor device 102. For example, the signal may be monitored during the full wear time and the PPG sensor device 102 may be configured to search for changes in the signal response such as timing for when the response is seen, amplitude of the response, area under the curve, and/or a lack of a designated signal response.

When a new infusion set is placed, the PPG sensor device 102 may generate, store, and monitor how long after an insulin dose event as communicated from a connected medical device 104 a peak 216 can be detected as well as an associated peak amplitude and/or area under the curve of the peak. Such parameters may be recorded for each subsequent programmed insulin dose and the medical device efficiency detection system 100 may be configured to monitor for changes to indicate a reduction in efficiency of insulin delivery to the user 110. Such changes may include delay in insulin dose peak (e.g., increased time to peak), reduction in amplitude for a given dose amount or an area under the curve for a given dose amount below a certain threshold (e.g. 5 second delay to peak from original dose event, 80% of original peak amplitude/area under the curve). Detection of such changes may operate to trigger an alarm condition by the medical device efficiency detection system 100 to notify the user 110 that an infusion set at an infusion site 108 being monitored is nearing or has passed an associated operational wear time and should be replaced soon. It is to be understood that the thresholds applied and monitored may vary by patient depending on patient factors for the user 110, such as level of control necessary for the patient, skill of patient with adjusting basal and bolus amounts to counteract infusion set wear, and the like.

In embodiments of the processes 400, 500, the medical device 104 may be an insulin delivery device, and the therapy treatment may include an insulin bolus. The insulin delivery device may be one of an insulin pump, an insulin injection pen, an insulin inhaler, or an insulin shot. When the insulin dosing occurs from the insulin injection pen, the insulin injection pen may be a wirelessly connected pen configured to transmit dosing quantity and timing to a monitoring device at which other disease relevant data is being captured. The insulin event may be captured from a sensor within the insulin injection pen configured to track a portion of the mechanical movement of an injection action or an insulin level change in a cartridge of the insulin injection pen. However, such a mechanical movement action may be indistinguishable from a priming of the insulin injection pen after a new cartridge has been inserted into the insulin injection pen. The PPG sensor device 102 may be used to distinguish such priming events and confirm delivery of insulin via the insulin injection pen rather than a priming action to avoid giving a false positive of an insulin event, and thus may more accurately verify actual injections of insulin by the medical device 104 before the data is shared with the monitoring device.

Thus, when the medical device 104 is an insulin injection pen, a communicatively connected PPG sensor device 102 located on the user 110 may monitor the spectral signal for a predefined period of time after a detected pen injection movement. The PPG sensor device 102 may thus be used to determine whether insulin has actually been injected into the user or if a monitored movement was rather a priming air shot injection movement, in which case the system 300 may be configured to record the monitored movement in the monitoring device as a priming movement (rather than an insulin delivery movement) or be configured to not recording the determining priming movement at all. In embodiments in which the insulin injection pen is not a smart pen or wirelessly connected pen, a communicatively connected PPG sensor device 102 may be used to identify an insulin injection event as described herein and send a notification signal to a monitoring device of the identified insulin injection event. At the monitoring device, and upon receipt of the notification signal, the user 110 may be prompted to provide additional input, such as to acknowledge the injection and provide specific information, such as the number of units, type of insulin, time of injection, and similar injection details.

Further, as described above, the system 300 may be configured to filter the signal response with an applied filter. The applied filter may be one of a bandpass filter and a notch filter to reduce noise. The bandpass filter may be configured to admit frequencies within a determined band, allowing those frequencies to pass and others below or above those admitted frequencies to be rejected. The notch filter may be configured to act as a bandstop filter to alternatively reject frequencies within a determined band while admitting other frequencies below or above the rejected frequencies. The signal response may normalized and scaled, and the applied filter may remove a corresponding DC portion.

In embodiments, the PPG sensor device 102 may be used with the medical device efficiency detection system 100 to determine the suitability of the underlying tissue of an infusion site 108 before an infusion set of the medical device 104 is inserted at the infusion site 108 and set. Using the PPG sensor device 102, the user 110 can analyze blood flow in the desired infusion site 108 before the medical device 104 is inserted to determine whether the infusion site 108 includes undesired abnormalities affecting sufficiency as an infusion site 108 for efficient treatment delivery such as scar tissue. Based on the PPG characteristics and signal quality as detected by the PPG sensor device 102 and described further below in FIG. 8, a determination can be made on the suitability of the infusion site 108 for insulin infusion before the infusion site 108 is placed or even whether other more suitable infusion sites 108 may be available.

Figure 8:
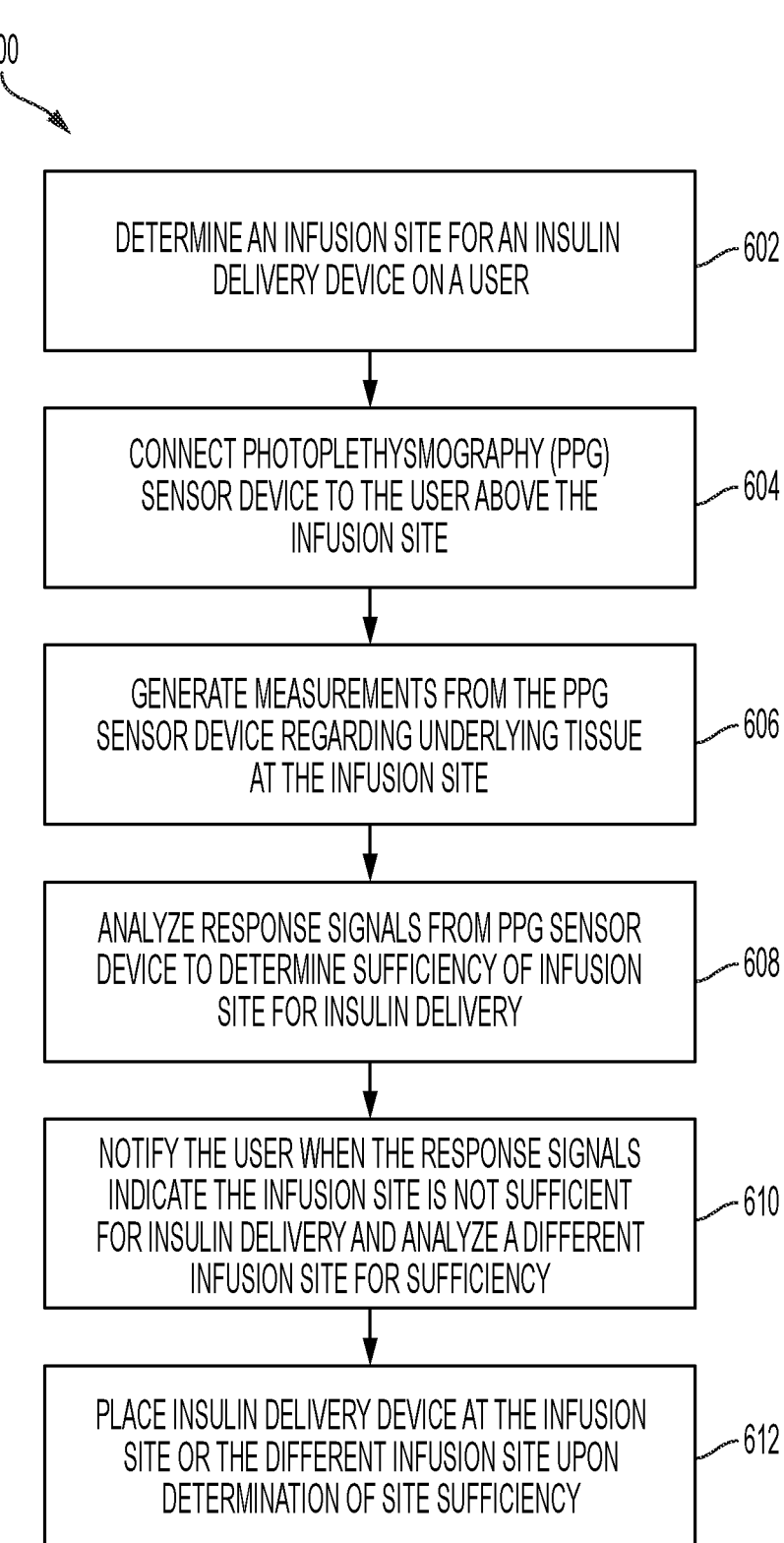
FIG. 8 is a flow chart of yet another process for using the systems of FIGS. 1 and 5, according to one or more embodiments shown and described herein.

Referring to FIG. 8, a process 600 is shown for using the medical device efficiency detection system 100 of FIG. 1 with the system 300 of FIG. 5, which implements the process 600 as described herein, to test whether an infusion site 108 is sufficient for insulin delivery. In embodiments, the medical device efficiency detection system 100 may include PPG sensor device 102, a processor 304 communicatively coupled to the PPG sensor device 102, a memory 306 communicatively coupled to the processor 304, and machine readable instructions stored in the memory 306. The machine readable instructions may cause the medical device efficiency detection system 100 to perform the process 600 when executed by the processor 304.

With respect to the process 600, in block 602, an infusion site 108 is determined for use by the medical device 104, such as to delivery insulin as an insulin delivery device to the user 110 at the infusion site 108. The infusion site 108 may be tested for sufficiency of insulin delivery prior to delivering insulin to the user 110 through the process 600.

In block 604, the PPG sensor device 102 is connected to the user 110 above the infusion site 108 determined for testing. In embodiments, the system 300 is configured to use the PPG sensor device 102 disposed over the infusion site 108 to be tested of the user 110, the infusion site 108 being the location of the user 110 at which the medical device 104 is to administer a therapy treatment.

In block 606, measurements from the PPG sensor device 102 regarding the underlying tissue and vasculature at the tested infusion site 108 may be generated, such as via the signals depicted of underlying tissue and vasculature in the diagram 270 of FIG. 4. Thus, the system 300 may be configured to generate signal measurements from the PPG sensor device 102 with respect to tissue and vasculature underlying the infusion site 108 that is being tested for sufficiency.

In block 608, response signals generated by PPG sensor device 102 may be analyzed to determine sufficiency of the infusion site 108 tested for insulin delivery. The system 300 may thus be configured to determine whether the signal measurements are within a sufficient signal range such that the infusion site 108 being tested is sufficient for delivery of the therapy treatment by the medical device 104.

In block 610, the user 110 may be notified when the response signals indicate that the infusion site 108 being tested is not sufficient for insulin delivery such that a different infusion site 108 is analyzed for sufficiency through the process 600 until an infusion site 108 is tested that is sufficient for insulin delivery. Thus, in embodiments, the system 300 may be configured to transmit an alert when the signal measurements are not within the sufficient signal range to indicate the infusion site 108 being tested is insufficient for delivery of the therapy treatment by the medical device 104.

When the signal measurements of the infusion site are not within the sufficient signal range, the PPG sensor device 102 may be disposed over one or more other infusion sites 108 to analyze respective signal measurements until one of the signal measurements of the one or more other infusion sites are within the sufficient signal range. The medical device efficiency detection system 100 to implement the process 600 may further include the medical device 104 configured to administer the therapy treatment, and the processor 304 may be communicatively coupled to the PPG sensor device 102 and the medical device 104

The system 300 may be configured to transit instructions to, when the signal measurements of the infusion site 108 or one of the signal measurements of the one or more other infusion sites 108 are within the sufficient signal range to indicate a sufficient infusion site, place the medical device 104 at the sufficient infusion site. The treatment therapy may then be delivered to the user 110 at the sufficient infusion site 108 using the medical device 104. For example, in block 612, the medical device 104 may be an insulin delivery device placed at the infusion site 108 or another tested infusion site 108 determined to sufficient for insulin delivery through the process 600 upon such determination of site sufficiency.

In embodiments, a handheld PPG sensor device 102 may either be incorporated into the medical device 104, which may be infusion set or pump, or may be incorporated into a separate dedicated infusion set placement sensor. Prior to placement of a new infusion set at an infusion site 108, the handheld PPG sensor device 102 may be passed across potential infusion sites 108 of the user 110, such as at the abdomen, posterior arms, chest, thighs or other suitable injection areas, to identify an optimal infusion site 108. Furthermore, a calibration of the PPG sensor device 102 may be conducted at least upon first use by the user 110 to determine the particular tissue characteristics of the user 110 and establish spectral baselines before an optimal site may be detected as an infusion site 108. By way of example, and not as a limitation, the user 110 may be instructed to scan an area on the abdomen by the PPG sensor device 102 where the user 110 has had predictable and consistent insulin delivery experience and then on other areas where sub-optimal insulin absorption would be expected, such as areas with higher fat or denser tissue, to aid in calibrating the PPG sensor device 102 and identifying sites as sufficient or insufficient sites by the PPG sensor device 102.

The PPG sensor device 102 may be placed on the tested infusion site 108 for a period of time such as a few seconds to gather a signal representative of local underlying tissue and vasculature of the tested infusion site 108 before giving an indication either directly on handheld PPG sensor device 102 or on another connected device of the suitability of the tested infusion site 108 as described herein. The indication may be binary as a textual signal or other visual signal (e.g., good or not good, green or red light) or a higher resolution indication indicative of a degree to which the site is suitable for optimal insulin delivery (e.g., a visual indication of low, medium, high, 1-10, or similar rank based indication). After identifying an infusion site 108 as a suitable injection site, the user may proceed with placing the new infusion set as the medical device 104 at the infusion site 108 and delivering insulin via the medical device 104 to the user 110.

Thus, the medical device efficiency detection system 100 and system 300 described herein may be configured to non-invasively detect when insulin is not properly delivered to the user 110 by the medical device 104 for diabetics, provide algorithm and control loop to compare response from multiple inputs to determine if insulin was actually delivered, and provide inter-device communication for exchanging data to determine if insulin was delivered. Further, the medical device efficiency detection system 100 and system 300 may be configured to implement a control loop to compare insulin absorption effectiveness over time and create a personalized infusion site wear time for an infusion site 108 to more efficiently and effectively use the infusion site 108 to deliver insulin. The medical device efficiency detection system 100 and system 300 may further be configured to be used to scan a tissue area before an infusion set of a medical device 104 is inserted at an infusion site 108 to determine suitableness of the infusion site 108 for insulin infusion based on sub-cutaneous and non-visible properties as analyzed as described herein by the PPG sensor device 102 of the medical device efficiency detection system 100.

Items Listing

Item 1. A medical device efficiency detection system may include a PPG sensor device, a medical device configured to administer a therapy treatment, a processor communicatively coupled to the PPG sensor device and the medical device, a memory communicatively coupled to the processor, and machine readable instructions stored in the memory. The machine readable instructions may cause the medical device efficiency detection system to perform at least the following when executed by the processor: communicatively connect the PPG sensor device and the medical device, deliver the therapy treatment to a user at an infusion site through the medical device, receive a notification at the PPG sensor device from the medical device upon delivery of the therapy treatment, use the PPG sensor device to search for a signal response of the user based on the notification within a period of time to generate a response signal indicative of therapy treatment delivery, and transmit an alert when the response signal is not generated in the period of time indicative of a failure to detect sufficient therapy treatment delivery.

Item 2. The medical device efficiency detection system of Item 1, wherein the machine readable instructions further include instructions to transmit the alert when the response signal is generated after a delay period in the period of time.

Item 3. The medical device efficiency detection system of Item 1 or Item 2, wherein the machine readable instructions further include instructions to transmit the alert when the response signal generated in the period of time is under a threshold value.

Item 4. The medical device efficiency detection system of Item 3, wherein when the response signal generated is under the threshold value, the alert includes an indication to move the infusion site to another location on the user.

Item 5. The medical device efficiency detection system of any of Item 1 to Item 4, wherein the medical device is an insulin delivery device and the therapy treatment is an insulin bolus.

Item 6. The medical device efficiency detection system of Item 5, wherein the insulin delivery device is one of an insulin pump, an insulin injection pen, an insulin inhaler, or an insulin shot.

Item 7. The medical device efficiency detection system of any of Item 1 to Item 6, wherein the machine readable instructions further include instructions to filter the signal response with an applied filter.

Item 8. The medical device efficiency detection system of Item 7, wherein the applied filter comprises one of a bandpass filter and a notch filter to reduce noise.

Item 9. The medical device efficiency detection system of any of Item 1 to Item 8, wherein the signal response is normalized and the applied filter removes a corresponding DC portion.

Item 10. The medical device efficiency detection system of any of Item 1 to Item 9, wherein the PPG sensor device is a separate wearable device configured to be disposed at an area on the user remote from the infusion site.

Item 11. The medical device efficiency detection system of Item 10, wherein the PPG sensor device is a wristband, a ring, a fingerclip, an adhesive patch, a toe clip, ear buds, earrings, or a forehead band.

Item 12. The medical device efficiency detection system of Item 10, wherein the PPG sensor device is a mobile smart device, wherein a camera and flash of the mobile smart device are configured to act as a photodiode and light source of the PPG sensor device respectively.

Item 13. The medical device efficiency detection system of any of Item 1 to Item 9, wherein the PPG sensor device is integrated with the medical device.

Item 14. A medical device efficiency detection system may include a PPG sensor device, a medical device configured to administer a therapy treatment, a processor communicatively coupled to the PPG sensor device and the medical device, a memory communicatively coupled to the processor, and machine readable instructions stored in the memory. The machine readable instructions may cause the medical device efficiency detection system to perform at least the following when executed by the processor: communicatively connect the PPG sensor device and the medical device, deliver the therapy treatment to a user at an infusion site through the medical device, receive a notification at the PPG sensor device from the medical device upon delivery of the therapy treatment, use the PPG sensor device to search for a signal response of the user based on the notification within a period of time to generate a response signal indicative of therapy treatment delivery, and transmit an alert when the response signal is not generated in the period of time indicative of a failure to detect sufficient therapy treatment delivery, when the response signal is generated after a delay period in the period of time, when the response signal generated in the period of time is under a threshold value, or combinations thereof.

Item 15. The medical device efficiency detection system of Item 14, wherein when the response signal generated is under the threshold value, the alert comprises an indication to move the infusion site to another location on the user.

Item 16. The medical device efficiency detection system of Item 14 or Item 15, wherein the PPG sensor device is a separate wearable device configured to be disposed at an area on the user remote from the infusion site.

Item 17. The medical device efficiency detection system of Item 14 or Item 15, wherein the PPG sensor device is integrated with the medical device.

Item 18. A medical device efficiency detection system may include a PPG sensor device, a processor communicatively coupled to the PPG sensor device, a memory communicatively coupled to the processor, and machine readable instructions stored in the memory. The machine readable instructions may cause the medical device efficiency detection system to perform at least the following when executed by the processor: dispose the PPG sensor device over an infusion site of a user at which a medical device is to administer a therapy treatment, generate signal measurements from the PPG sensor device with respect to tissue and vasculature underlying the infusion site, determine whether the signal measurements are within a sufficient signal range such that the infusion site is sufficient for delivery of the therapy treatment by the medical device, and transmit an alert when the signal measurements are not within the sufficient signal range to indicate the infusion site is insufficient for delivery of the therapy treatment by the medical device.

Item 19. The medical device efficiency detection system of Item 18, wherein the machine readable instructions further include instructions to, when the signal measurements of the infusion site are not within the sufficient signal range, dispose the PPG sensor device over one or more other infusion sites to analyze respective signal measurements until one of the signal measurements of the one or more other infusion sites are within the sufficient signal range.

Item 20. The medical device efficiency detection system of Item 19, further including the medical device configured to administer the therapy treatment, the processor communicatively coupled to the PPG sensor device and the medical device. The machine readable instructions further include instructions to, when the signal measurements of the infusion site or one of the signal measurements of the one or more other infusion sites are within the sufficient signal range to indicate a sufficient infusion site, place the medical device at the sufficient infusion site, and deliver the treatment therapy to the user at the sufficient infusion site using the medical device.

It is noted that recitations herein of a component of the present disclosure being "configured" or "programmed" in a particular way, to embody a particular property, or to function in a particular manner, are structural recitations, as opposed to recitations of intended use. More specifically, the references herein to the manner in which a component is "configured" or "programmed" denotes an existing physical condition of the component and, as such, is to be taken as a definite recitation of the structural characteristics of the component.

It is noted that the terms "substantially" and "about" and "approximately" may be utilized herein to represent the inherent degree of uncertainty that may be attributed to any quantitative comparison, value, measurement, or other representation. These terms are also utilized herein to represent the degree by which a quantitative representation may vary from a stated reference without resulting in a change in the basic function of the subject matter at issue.

While particular embodiments have been illustrated and described herein, it should be understood that various other changes and modifications may be made without departing from the spirit and scope of the claimed subject matter. Moreover, although various aspects of the claimed subject matter have been described herein, such aspects need not be utilized in combination. It is therefore intended that the appended claims cover all such changes and modifications that are within the scope of the claimed subject matter.

What is claimed is:

1. A medical device efficiency detection system comprising:

a photoplethysmography (PPG) sensor device;

a medical device configured to administer a therapy treatment;

a processor communicatively coupled to the PPG sensor device and the medical device;

a memory communicatively coupled to the processor; and machine readable instructions stored in the memory that cause the medical device efficiency detection system to perform at least the following when executed by the processor:

communicatively connect the PPG sensor device and the medical device;

deliver the therapy treatment to a user at an infusion site through the medical device;

receive a notification at the PPG sensor device from the medical device upon delivery of the therapy treatment;

use the PPG sensor device to search for a signal response of the user based on the notification within a period of time to generate a response signal indicative of therapy treatment delivery; and transmit an alert when the response signal is not generated in the period of time indicative of a failure to detect sufficient therapy treatment delivery.

2. The medical device efficiency detection system of claim 1, wherein the machine readable instructions further comprise instructions to transmit the alert when the response signal is generated after a delay period in the period of time.

3. The medical device efficiency detection system of claim 1, wherein the machine readable instructions further comprise instructions to transmit the alert when the response signal generated in the period of time is under a threshold value.

4. The medical device efficiency detection system of claim 3, wherein when the response signal generated is under the threshold value, the alert comprises an indication to move the infusion site to another location on the user.

5. The medical device efficiency detection system of claim 1, wherein the medical device comprises an insulin delivery device and the therapy treatment comprises an insulin bolus.

6. The medical device efficiency detection system of claim 5, wherein the insulin delivery device comprises one of an insulin pump, an insulin injection pen, an insulin inhaler, or an insulin shot.

7. The medical device efficiency detection system of claim 1, wherein the machine readable instructions further comprise instructions to filter the signal response with an applied filter.

8. The medical device efficiency detection system of claim 7, wherein the applied filter comprises one of a bandpass filter and a notch filter to reduce noise.

9. The medical device efficiency detection system of claim 7, wherein the signal response is normalized and the applied filter removes a corresponding DC portion.

10. The medical device efficiency detection system of claim 1, wherein the PPG sensor device comprises a separate wearable device configured to be disposed at an area on the user remote from the infusion site.

11. The medical device efficiency detection system of claim 10, wherein the PPG sensor device comprises a wristband, a ring, a fingerclip, an adhesive patch, a toe clip, ear buds, earrings, or a forehead band.

12. The medical device efficiency detection system of claim 10, wherein the PPG sensor device comprises a mobile smart device, wherein a camera and flash of the mobile smart device are configured to act as a photodiode and light source of the PPG sensor device respectively.

13. The medical device efficiency detection system of claim 1, wherein the PPG sensor device is integrated with the medical device.

14. A medical device efficiency detection system comprising:

a photoplethysmography (PPG) sensor device;

a medical device configured to administer a therapy treatment;

a processor communicatively coupled to the PPG sensor device and the medical device;

a memory communicatively coupled to the processor; and machine readable instructions stored in the memory that cause the medical device efficiency detection system to perform at least the following when executed by the processor:

communicatively connect the PPG sensor device and the medical device;

deliver the therapy treatment to a user at an infusion site to which the medical device is connected;

receive a notification at the PPG sensor device from the medical device upon delivery of the therapy treatment;

use the PPG sensor device to search for a signal response of the user based on the notification within a period of time to generate a response signal indicative of therapy treatment delivery; and transmit an alert when the response signal is not generated in the period of time indicative of a failure to detect sufficient therapy treatment delivery, when the response signal is generated after a delay period in the period of time, when the response signal generated in the period of time is under a threshold value, or combinations thereof.

15. The medical device efficiency detection system of claim 14, wherein when the response signal generated is under the threshold value, the alert comprises an indication to move the infusion site to another location on the user.

16. The medical device efficiency detection system of claim 14, wherein the PPG sensor device comprises a separate wearable device configured to be disposed at an area on the user remote from the infusion site.

17. The medical device efficiency detection system of claim 14, wherein the PPG sensor device is integrated with the medical device.

18. A medical device efficiency detection system comprising:

a photoplethysmography (PPG) sensor device;

a processor communicatively coupled to the PPG sensor device;

a memory communicatively coupled to the processor; and machine readable instructions stored in the memory that cause the medical device efficiency detection system to perform at least the following when executed by the processor:

dispose the PPG sensor device over an infusion site of a user at which a medical device is to administer a therapy treatment;

generate signal measurements from the PPG sensor device with respect to tissue and vasculature underlying the infusion site;

determine whether the signal measurements are within a sufficient signal range such that the infusion site is sufficient for delivery of the therapy treatment by the medical device; and transmit an alert when the signal measurements are not within the sufficient signal range to indicate the infusion site is insufficient for delivery of the therapy treatment by the medical device.

19. The medical device efficiency detection system of claim 18, wherein the machine readable instructions further comprise instructions to, when the signal measurements of the infusion site are not within the sufficient signal range, dispose the PPG sensor device over one or more other infusion sites to analyze respective signal measurements until one of the signal measurements of the one or more other infusion sites are within the sufficient signal range.

20. The medical device efficiency detection system of claim 19, further comprising the medical device configured to administer the therapy treatment, the processor communicatively coupled to the PPG sensor device and the medical device, wherein the machine readable instructions further comprise instructions to:

when the signal measurements of the infusion site or one of the signal measurements of the one or more other infusion sites are within the sufficient signal range to indicate a sufficient infusion site, place the medical device at the sufficient infusion site; and deliver the therapy treatment to the user at the sufficient infusion site using the medical device.

* * * * *